US00PP30488P2

(12) United States Plant Patent
Heuger

(10) Patent No.: US PP30,488 P2
(45) Date of Patent: May 7, 2019

(54) ***HELLEBORUS* PLANT NAMED 'COSEH 4600'**

(50) Latin Name: ***Helleborus* x *ericsmithii* X *Helleborus* x *hybridus***
Varietal Denomination: COSEH 4600

(71) Applicant: Josef Heuger, Glandorf (DE)

(72) Inventor: Josef Heuger, Glandorf (DE)

( * ) Notice: Subject to any disclaimer, the term of this patent is extended or adjusted under 35 U.S.C. 154(b) by 0 days.

(21) Appl. No.: 15/732,562

(22) Filed: Nov. 27, 2017

(51) Int. Cl.
*A01H 5/02* (2018.01)

(52) U.S. Cl.
USPC ..... Plt./439

(58) Field of Classification Search
USPC ..... Plt./263.1, 439
See application file for complete search history.

*Primary Examiner* — Susan McCormick Ewoldt
*Assistant Examiner* — Karen M Redden
(74) *Attorney, Agent, or Firm* — C. A. Whealy

(57) ABSTRACT

A new and distinct cultivar of *Helleborus* plant named 'COSEH 4600', characterized by its relatively tall, upright and mounding plant habit; moderately vigorous growth habit; dark green-colored leaves; freely flowering habit; single dark greyed purple-colored flowers; and good garden performance.

2 Drawing Sheets

Botanical designation: *Helleborus* x *ericsmithii* X *Helleborus* x *hybridus*.

Cultivar denomination: 'COSEH 4600'.

BACKGROUND OF THE INVENTION

The present invention relates to a new and distinct cultivar of *Helleborus* plant, botanically known as *Helleborus* x *ericsmithii* X *Helleborus* x *hybridus* and hereinafter referred to by the name 'COSEH 4600'.

The new *Helleborus* plant is a product of a planned breeding program conducted by the Inventor in Glandorf, Germany. The objective of the breeding program was to create new uniform *Helleborus* plants with unique and attractive plant habit, leaf and flower coloration and resistance to pests common to *Helleborus* plants.

The new *Helleborus* plant originated from a cross-pollination conducted by the Inventor in Glandorf, Germany in 2012 of a unnamed selection of *Helleborus* x *ericsmithii*, not patented, as the female, or seed parent and an unnamed selection of *Helleborus* x *hybridus*, not patented, as the male, or pollen parent. The new *Helleborus* plant was discovered and selected by the Inventor as a single flowering plant from within the progeny of the stated cross-pollination grown in a controlled greenhouse environment in Glandorf, Germany in 2014.

Asexual reproduction of the new *Helleborus* plant by divisions in a controlled environment in Glandorf, Germany since 2015 has shown that the unique features of this new *Helleborus* plant are stable and reproduced true to type in successive generations.

SUMMARY OF THE INVENTION

Plants of the new *Helleborus* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'COSEH 4600'. These characteristics in combination distinguish 'COSEH 4600' as a new and distinct *Helleborus* plant:

1. Relatively tall, upright and mounded plant habit.
2. Moderately vigorous growth habit.
3. Dark green-colored leaves.
4. Moderately freely flowering habit.
5. Single dark greyed purple-colored flowers.
6. Good garden performance.

Plants of the new *Helleborus* and the parent selections differ primarily in flower color as plants of the female parent selection have flowers that are pink in color and plants of the male parent selection have flowers that are red in color. In addition, plants of the new *Helleborus* are taller than plants of the female and male parent selections.

Plants of the new *Helleborus* can be compared to plants of *Helleborus* x *hybridus* 'ABCRD02', disclosed in U.S. Plant Pat. No. 24,720. In side-by-side comparisons, plants of the new *Helleborus* differ primarily from plants of 'ABCRD02' in flower color as plants of 'ABCRD02' have flowers that are lighter purple in color.

BRIEF DESCRIPTION OF THE PHOTOGRAPHS

The accompanying colored photographs illustrate the overall appearance of the new *Helleborus* plant showing the colors as true as it is reasonably possible to obtain in colored reproductions of this type. Colors in the photographs may differ slightly from the color values cited in the detailed botanical description which accurately describe the colors of the new *Helleborus* plant.

The photograph on the first sheet is a side perspective view of a typical flowering plant of 'COSEH 4600' grown in a container.

The photograph on the second sheet is a close-up view of a typical flower of 'COSEH 4600'.

DETAILED BOTANICAL DESCRIPTION

The aforementioned photographs and following observations, measurements and values describe plants grown during the winter in 17-cm containers in a glass-covered greenhouse in Glandorf, Germany and under cultural practices typical of commercial *Helleborus* production. During the production of the plants, day temperatures ranged from 12° C. to 24° C. and night temperatures ranged from 3° C. to 18° C. Plants were 14 months old when the photographs and the description were taken. In the following description, color references are made to The Royal Horticultural Society Colour Chart, 2015 Edition, except where general terms of ordinary dictionary significance are used.

Botanical classification: *Helleborus* x *ericsmithii* X *Helleborus* x *hybridus* 'COSEH 4600'.

Parentage:

*Female, or seed, parent*.—Unnamed selection of *Helleborus* x *ericsmithii*, not patented.

*Male, or pollen, parent*.—Unnamed selection of *Helleborus* x *hybridus*, not patented.

Propagation:

*Type*.—In vitro rhizome culture.

*Time to initiate roots, winter*.—About two months at temperatures about 12° C.

*Time to produce a rooted young plant, winter*.—About six months at temperatures ranging from 4° C. to 15° C.

*Root description*.—Thick to thin, fleshy; typically white to brown in color, actual color of the roots is dependent on substrate composition, water quality, fertilizer type and formulation, substrate temperature and physiological age of roots.

*Rooting habit*.—Sparse.

Plant description:

*Plant and growth habit*.—Herbaceous perennial; relatively tall, upright and mounding plant habit with flowers held above the foliar plane; plant shape, roughly flattened globular; moderately vigorous growth habit; moderate growth rate.

*Plant height, soil level to top of foliar plane*.—About 32 cm.

*Plant height, soil level to top of flowers*.—About 42.8 cm.

*Plant diameter* (*area of spread*).—About 43.1 cm.

Leaf description:

*Arrangement*.—Leaves arranged in a basal rosette; leaves palmately compound with typically five leaflets per leaf.

*Leaf length*.—About 19.5 cm.

*Leaf width*.—About 18.4 cm.

*Leaflet length*.—About 12.7 cm.

*Leaflet width*.—About 7.2 cm.

*Leaf shape*.—Palmate; reniform in outline.

*Leaflet shape*.—Obovate to elliptic.

*Leaflet apex*.—Short apiculate to acute.

*Leaflet base*.—Attenuate.

*Leaflet margin*.—Coarsely serrate; moderately undulate.

*Leaflet texture and luster, upper surface*.—Slightly rugose, glabrous; moderately leathery; moderately glossy.

*Leaflet texture and luster, lower surface*.—Slightly rugose, glabrous; moderately leathery; slightly glossy.

*Leaflet venation pattern*.—Pinnate.

*Leaflet color*.—Developing leaflets, upper surface: Close to between NN137A and 147A. Developing leaflets, lower surface: Close to between N186C and N200A. Fully developed leaflets, upper surface: Close to darker than between 147A and N189A; venation, close to 147B. Fully developed leaflets, lower surface: Close to 143A to 143B; proximally tinged with close to between N186C and 200A; venation, close to 187B.

*Petioles*.—Length: About 14.4 cm. Diameter: About 5.5 mm to 6.5 mm. Strength: Strong. Texture and luster, upper and lower surfaces: Smooth, glabrous; moderately glossy. Color, upper and lower surfaces: Close to 144B; moderately to densely covered with small spots, close to 187A and 187B.

Flower description:

*Flower shape and habit*.—Single rotate flowers; arranged solitary or in small clusters with about five flowers each; moderately freely flowering habit with about 25 flowers developing per plant; flowers facing outwardly to nodding.

*Fragrance*.—None detected.

*Natural flowering season*.—Plants begin flowering about ten months after planting; plants flower during the winter in Germany.

*Flower longevity on the plant*.—About ten days; sepals persistent, other flower parts not persistent.

*Flower buds*.—Length: About 2.4 cm. Diameter: About 1.7 cm. Shape: Broadly ovoid. Texture and luster: Smooth, glabrous; matte. Color: Close to between N186C and 187A.

*Inflorescence height*.—About 23.6 cm.

*Inflorescence diameter*.—About 18.7 cm.

*Flower diameter*.—About 7.2 cm.

*Flower depth* (*height*).—About 3.8 cm.

*Petals*.—Transformed into nectaries.

*Sepals*.—Quantity and arrangement: About five, arranged in a single whorl. Length: About 5.5 cm. Width: About 5.3 cm. Shape: Broadly ovate to nearly orbicular, moderately to slightly concave. Apex: Obtuse. Base: Cuneate. Margin: Entire; very slightly undulate. Texture and luster, upper surface: Smooth, glabrous; matte. Texture and luster, lower surface: Smooth, glabrous; slightly glossy. Color: When opening, upper and lower surfaces: Close to N186C and slightly darker than N186C. Fully opened, upper surface: Close to between N186C and 187A. Fully opened, lower surface: Close to N186C tinged and marbled with close to 187A and 187B.

*Flower bracts*.—Quantity per flower: Typically two. Length: About 4.4 cm to 11 cm. Width: About 3 cm and 6.5 cm. Shape: Ovate. Apex: Acute. Base: Broadly cuneate. Margin: Serrate; slightly undulate. Color, upper surface: Darker than between NN137A and 147A. Color, lower surface: Darker than between N186C and 200A.

*Peduncles*.—Length: About 39.1 cm. Diameter: About 8 mm to 12 mm. Aspect: About 10° from vertical. Strength: Strong. Texture and luster: Smooth, glabrous; moderately glossy. Color: Close to 144C; flushed and densely covered with small spots, close to 187A to 187B.

*Pedicels*.—Length: About 6 cm. Diameter: About 3.5 mm to 4 mm. Aspect: About 35° from peduncle axis. Strength: Moderately strong. Texture and luster: Smooth, glabrous; glossy. Color: Close to between N186C and 200A.

*Reproductive organs*.—Stamens: Quantity per flower: About 90. Filament length: About 1.8 cm. Filament color: Close to N155B tinged with close to 186D. Anther shape: Reniform; basifixed. Anther size: About 1.75 mm by 3 mm. Anther color: Close to 1C. Pollen amount: Scarce. Pollen color: Close to 4D. Pistils: Quantity per flower: About four. Pistil length: About 1.5 cm. Stigma diameter: About 0.3 mm. Stigma shape: Club-shaped. Stigma color: Close to 157A. Style length: About 1.45 cm. Style color: Close to N186C. Ovary color: Close to N186C. Nectaries (transformed petals): Quantity per flower: About 12 to 14. Length: About 1.5 cm. Diameter: About 4 mm. Shape: Tubular, flattened. Texture and luster, inner and outer surfaces: Smooth, glabrous; matte. Color, immature, inner and outer surfaces: Close to N144A to N144B. Color, mature, inner and outer surfaces: Close to N144A; distally, close to 151B; distal color becoming closer to 153D with development.

*Seeds and fruits*.—Seed and fruit development have not been observed on plants of the new *Helleborus* to date.

Garden performance: Plants of the new *Helleborus* have been observed to have good garden performance and to tolerate rain, wind and to be suitable for USDA Hardiness Zones 5 through 9.

Pathogen & pest resistance: Plants of the new *Helleborus* have not been observed to be resistant to pathogens and pests common to *Helleborus* plants to date.

It is claimed:

1. A new and distinct *Helleborus* plant named 'COSEH 4600' as illustrated and described.

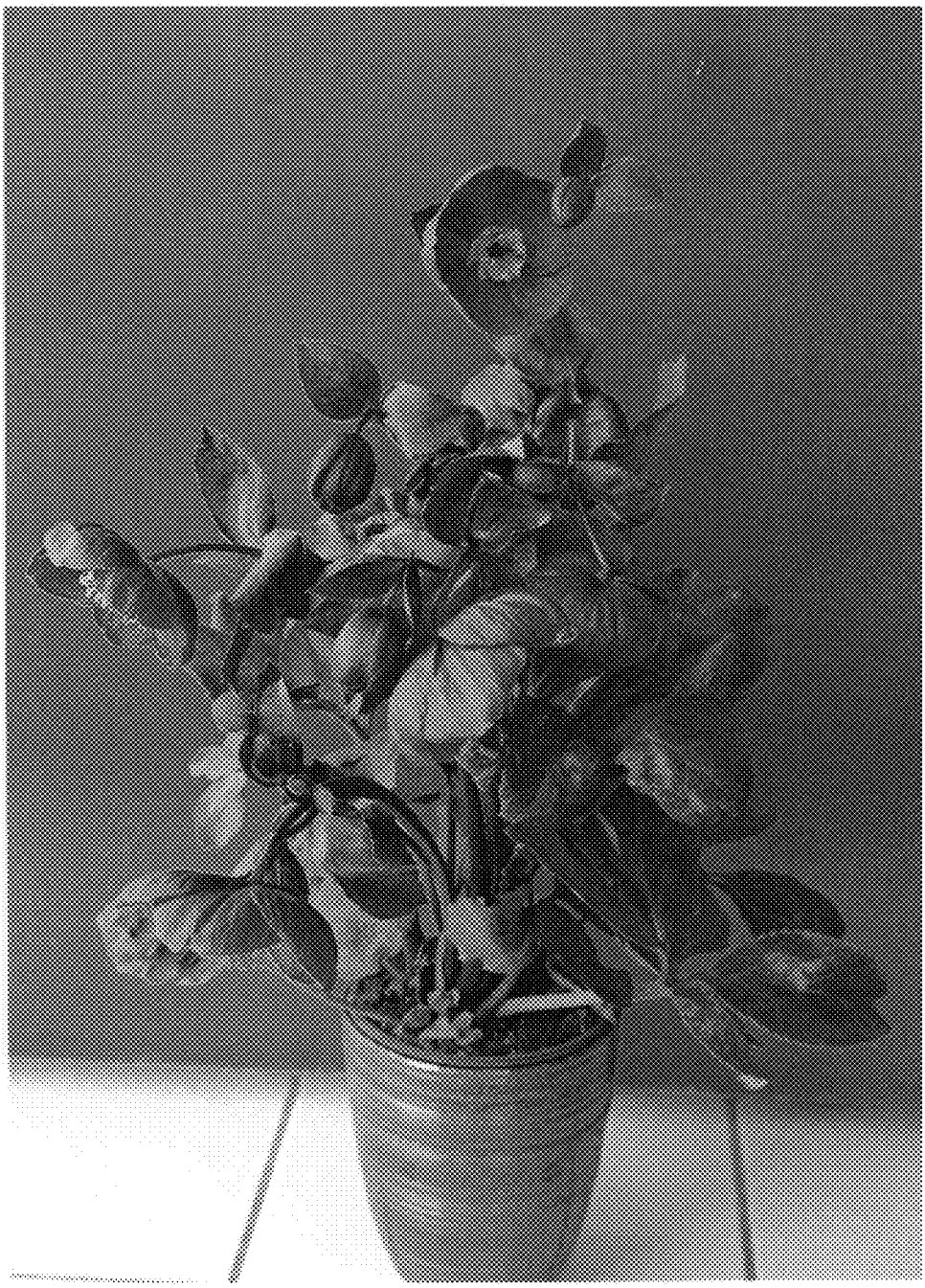

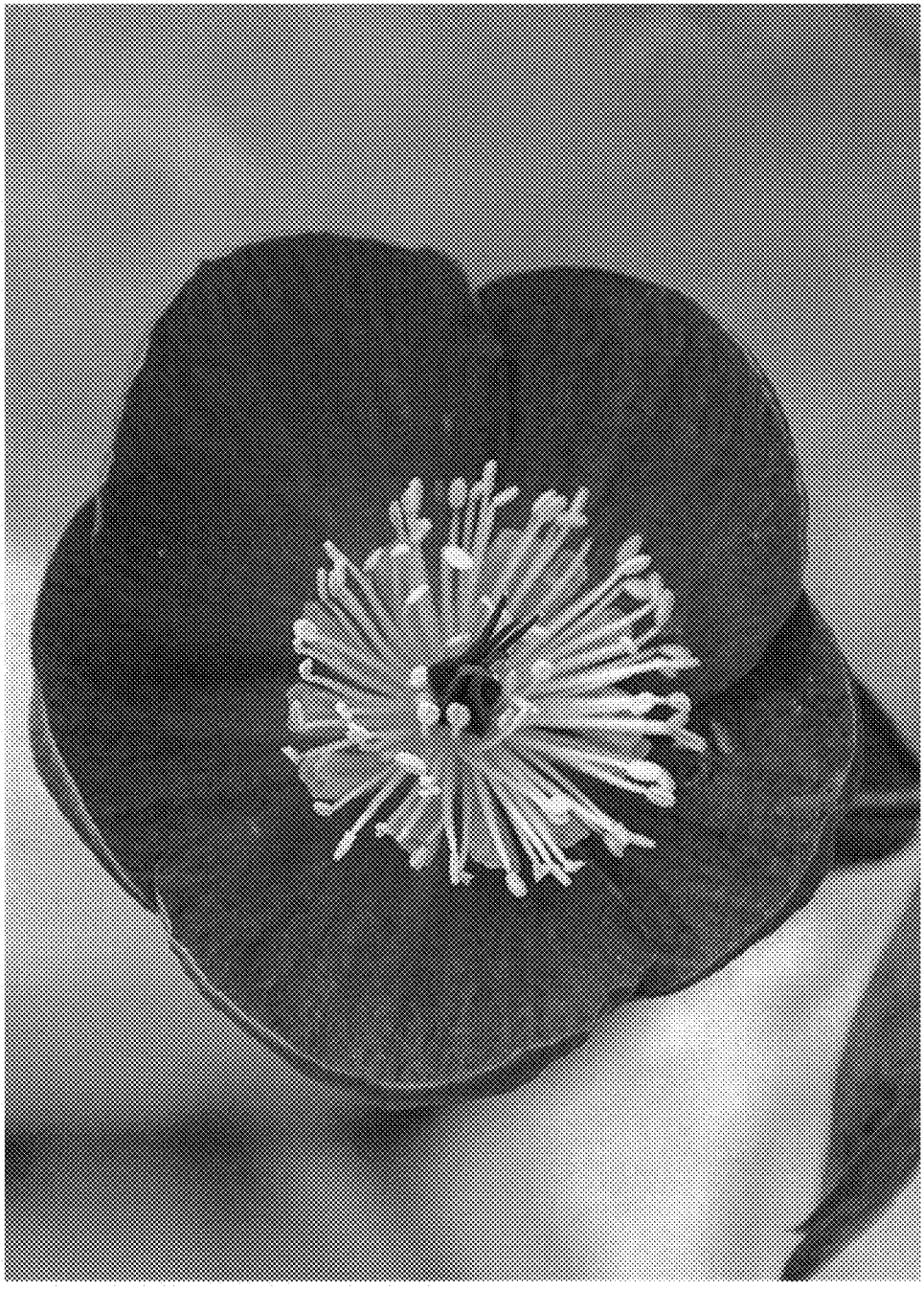

* * * * *